United States Patent [19]

Yoshida et al.

[11] Patent Number: 5,324,742

[45] Date of Patent: Jun. 28, 1994

[54] **ALDOSE REDUCTASE INHIBITOR OBTAINED FROM *CRUCIBULUM* SP. RF-3817**

[75] Inventors: Tadashi Yoshida, Osaka; Toshiyuki Kato, Hyogo; Yoshimi Kawamura; Koichi Matsumoto, both of Osaka; Hiroshi Itazaki, Hyogo, all of Japan

[73] Assignee: Shionogi & Co., Ltd., Osaka, Japan

[21] Appl. No.: 697,009

[22] Filed: May 8, 1991

[30] Foreign Application Priority Data

May 30, 1990 [JP] Japan .................... 2-142463

[51] Int. Cl.$^5$ ............... C07D 491/048; A61K 31/40; C12P 17/18; C12N 9/99
[52] U.S. Cl. .................... 514/411; 548/430; 435/184; 435/119
[58] Field of Search ............ 548/430; 514/411; 435/118, 171, 254; 424/93 Q

[56] References Cited

U.S. PATENT DOCUMENTS

| | | | |
|---|---|---|---|
| 3,812,112 | 5/1974 | Kimura et al. | 548/430 |
| 4,337,265 | 6/1982 | Treasurywala et al. | 548/512 |
| 4,503,236 | 3/1985 | Unangst | 548/430 |
| 4,695,571 | 9/1987 | Melvin | 514/411 |

FOREIGN PATENT DOCUMENTS

| | | |
|---|---|---|
| 0109866 | 5/1984 | European Pat. Off. . |
| 0222576 | 5/1987 | European Pat. Off. . |
| 0252713 | 1/1988 | European Pat. Off. . |

OTHER PUBLICATIONS

Sarges, Advances in Drug Research, vol. 18, pp. 139–175 (1989).
Horhammer et al, Arch. Pharm., vol. 292, pp. 113–125 (1959).

Primary Examiner—Joseph Paul Brust
Assistant Examiner—MarySusan H. Gabilan
Attorney, Agent, or Firm—Birch, Stewart, Kolasch & Birch

[57] ABSTRACT

The present invention relates to a novel aldose reductase inhibitor of the formula:

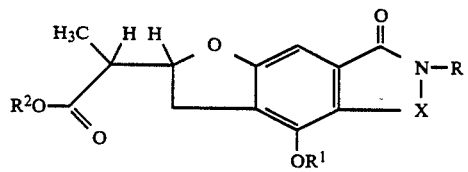

wherein
X is methylene or carbonyl;
R is

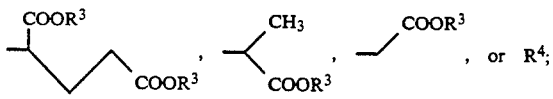

$R^1$, $R^2$, $R^3$, and $R^4$ each is hydrogen or lower alkyl, to a method for producing the inhibitor by culturing Crucibulum sp. RF-3817 or its variants, and to an agent for inhibiting an aldose reductase comprising the inhibitor.

11 Claims, 5 Drawing Sheets

ALDOSE REDUCTASE INHIBITOR OBTAINED FROM *CRUCIBULUM* SP. RF-3817

BACKGROUND OF THE INVENTION

1. Field of the Invention

The present invention relates to a novel aldose reductase inhibitor and a method for producing the same.

The novel compound of the invention is represented by the formula:

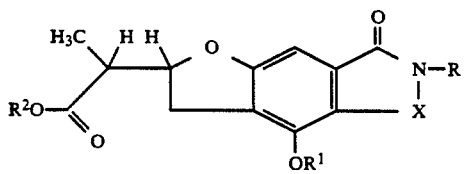

wherein
X is methylene or carbonyl;
R is

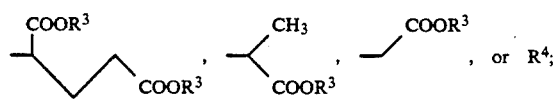

$R^1$, $R^2$, $R^3$, and $R^4$ each is hydrogen or lower alkyl.

2. Description of the Prior Art

The incidence rate of diabetes has hitherto increased and various complications thereof have become a quite serious problem. The complications of diabetes may be caused by, for example, accumulation of polyol (e.g., sorbitol), free radical peroxidation, and glycosylation of proteins at the site of lysine residues. An inhibitor for aldose reductase (abbreviated hereinafter as AR) relating to polyol accumulation is expected to serve as a medicine for diabetic complications, that is, diseases arising from diabetes such as diabetic neuropathy, diabetic cataract, diabetic keratopathy, diabetic retinopathy, and diabetic nephropathy. Although there have been many investigations into the development of such a medicine, development of more beneficial inhibitors is still necessary (see Reinhard Sages, Advances in Drug Research, 18, 139–175 (1989)). Typical examples of AR inhibitors include Quercitrin reported by Hörhammer et al. (see Arch Pharm., 292, 113 (1959)).

It has been revealed that AR as a rate-limiting enzyme in the metabolic pathway of polyol is present in blood vessels, peripheral nerves, lenses, retinae, and so forth, in which many complications of diabetes often occur. Therefore, the significance of AR became understood in relation to diabetes. In the state of glycophilia such as diabetes, a larger amount of glucose than is capable of being metabolized in the glycolysis system is present in cells and the metabolism of glucose in the metabolic pathway of polyol can readily be promoted because glucose is used as a substrate for AR. As a result, the abnormal accumulation of sorbitol is further enhanced. Sorbitol is a relatively stable substance; once the cells produce sorbitol, very little extracellular release of the sorbitol is found. The imbalance between the production and metabolism causes the intracellular accumulation of this sugar alcohol. This results in an increase in intracellular osmotic pressure and a lot of water remains in the cells, thereby making it impossible to maintain the normal function of the cells and exhibiting a disorder of the cells. If the AR activity is inhibited, the abnormal intracellular accumulation of sorbitol can be avoided, and there is a great possibility that the normal function of the cells can be maintained. Accordingly, the present inventors have made an effort to search compounds having an AR-inhibiting activity.

SUMMARY

The present invention relates to a compound of the formula(A);

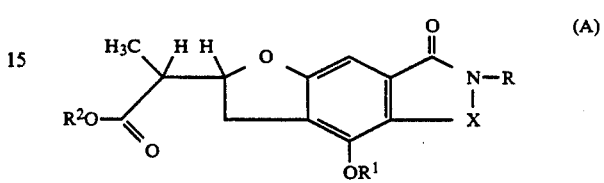

wherein
X is methylene or carbonyl;
R is

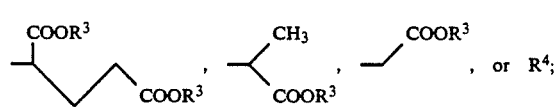

$R^1$, $R^2$, $R^3$, and $R^4$ each is hydrogen or lower alkyl, or the salt thereof,
preferably to the compound wherein R is

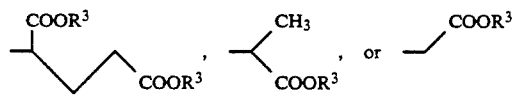

where
X is methylene;
R is

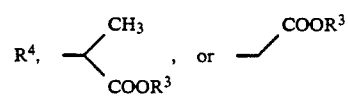

where
X is carbonyl, or the salt thereof,
and more preferably to the compound wherein $R^3$ or $R^4$ is hydrogen or the salt thereof.

This invention also relates to a method for producing the compound, which comprises culturing Crucibulum sp. RF-3817 or its variants which can produce a compound of the formula(B):

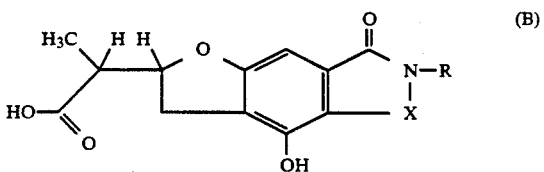

wherein R is

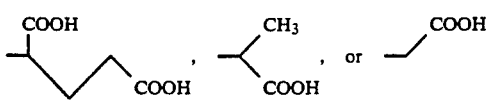

where
X is methylene;
R is

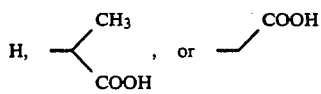

where X is carbonyl;
isolating the above mentioned compound from the cultured medium and optionally alkylating the compound. It further provides a pharmaceutical agent comprising the compound, as an effective ingredient, in association with a pharmaceutically acceptable, substantially non-toxic carrier or excipient, which inhibits an aldose reductase.

In the present invention, the lower alkyl groups include straight- or branched-methyl, ethyl, propyl, and butyl.

The compound of the present invention may be used as a medicine for diabetic complications such as diabetic neuropathy, diabetic cataract, diabetic keratopathy, diabetic retinopathy, and diabetic nephropathy, because of its aldose reductase-inhibiting activity.

DESCRIPTION OF THE PREFERRED EMBODIMENTS

Figure 1:
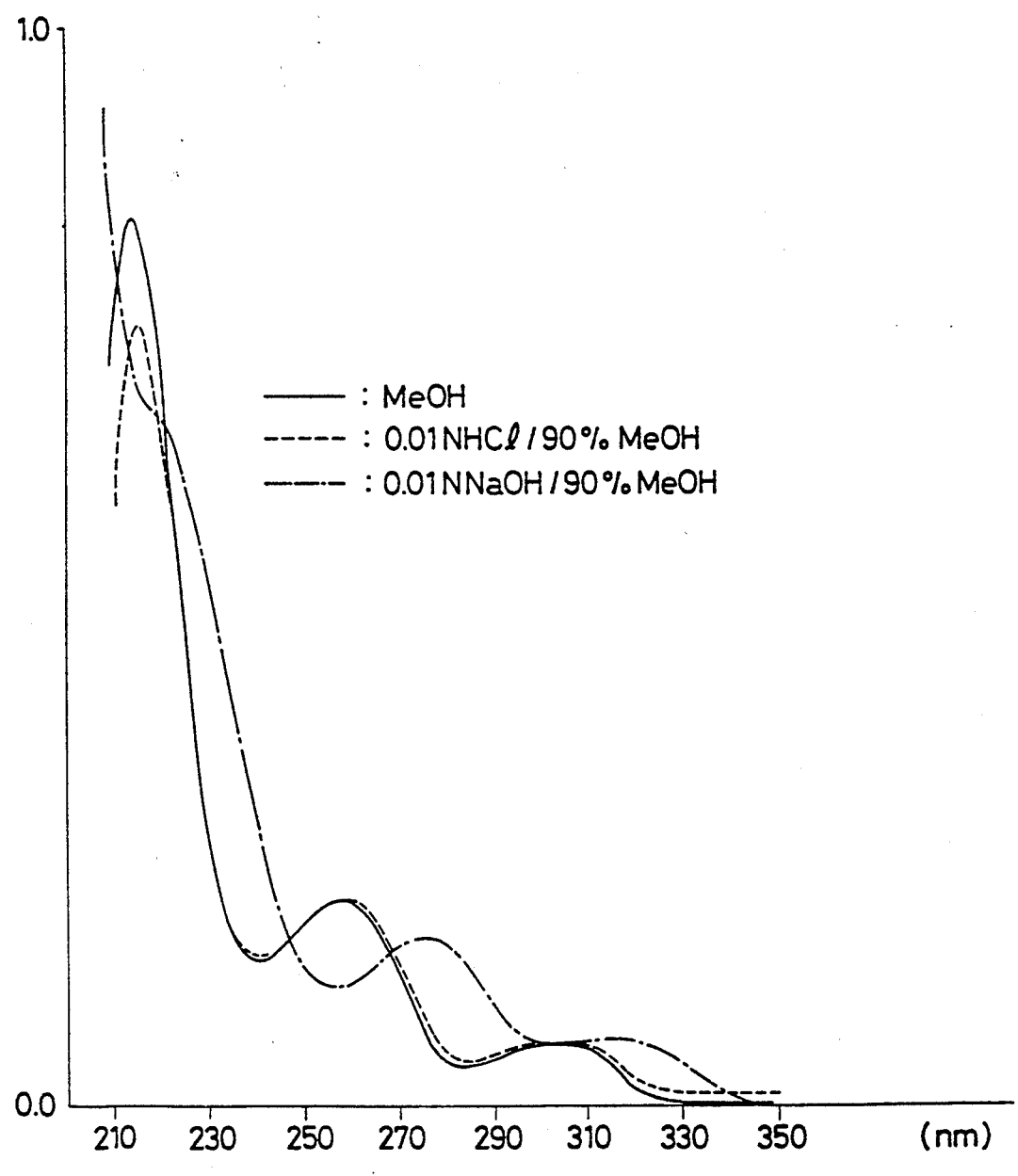
FIG. 1 is a UV spectrum of RD-01-A$_4$ of the present invention.

The strain RF-3817 of the genus Crucibulum capable of producing the compound of the present invention has the following properties.

Various Taxonomical Properties of the Strain RF-3817

The strain RF-3817 was isolated as follows. First, peridioles within the peridium formed on a rotten wood block were immersed in a solution of sodium hypochlorite for one minute, whereby the surface of the peridioles was sterilized. Then, the peridioles were washed with sterile water and the basidiospores formed within the peridioles were placed on an appropriate medium to isolate the strain. On the hyphae of the strain grown on the medium, clamp connections were observed, the width of each hypha being 1 to 5 μm.

The peridium of the strain formed on the rotten wood block is pyriform, 5 to 8 mm in height, 4 to 6 mm in diameter, and has an ocher color. In the upper portion of the peridium, there is an epiphragm having a pale yellowish-white color, which will dehisce when matured. Within the peridium, lenticular peridioles are observed. The peridioles, 1 to 1.5 mm in size, attached by funiculi to inner wall of peridium. Within the peridodioles, there are formed basidiospores, the size thereof being 3 to 5 by 7 to 10 μm.

These properties were compared with the characteristics of each of genera belonging to the order Nidulariales, the family Nidulariaceae, as described in H. J. Brodie, "The Bird's Nest Fungi," Univ. of Toronto Press, Toronto and Buffalo (1975), and Rokuya Imazeki & Tsugio Hongo, "Colored Illustrations of New Fungus in Japan, Vol. II, (1989)" Hoikusya Publishing Co., Ltd. According to the comparison, the strain of the present invention was identified as a strain of the genus Crucibulum and named Crucibulum sp. RF-3817. The strain of the present invention was deposited on May 9, 1990, under the terms of the Budapest Treaty with the Fermentation Research Institute, Agency of Industrial Science and Technology, 1-3, Higashi 1-chome Tsukuba-shi, Ibarakiken 305, and has been assigned "Crucibulum sp. RF-3817" with the Accession No, FERM BP-2888.

The following will describe a general method for producing the compound of the present invention.

The production can be performed using a medium composition and condition which are used in the ordinary production by fermentation. A typical medium usually contains carbon sources, nitrogen sources, inorganic salts, and others. If necessary, vitamins and precursors may also be added to the medium. As the carbon sources, for example, glucose, potato starch, dextrin, glycerol, molasses, and organic acids can be used alone or in a mixture thereof. As the nitrogen sources, for example, soybean powder, corn steep liquor, meat extract, yeast extract, cotton seed powder, peptone, wheat germ, ammonium sulfate, and ammonium nitrate can be used alone or in a mixture thereof. As the inorganic salts, for example, calcium carbonate, sodium chloride, potassium chloride, magnesium sulfate, copper sulfate, manganese chloride, zinc sulfate, cobalt chloride, and various phosphates can be used, and these inorganic salts are added to the medium whenever they are required.

The temperature of incubation which can be used is in a range of from about 20° to 40° C. with a temperature of from 25° to 32° C. being preferred. The time of incubation depends greatly upon the scale of fermentation and from about 7 to 10 days are required for mass production. In cases where vigorous foaming occurs during incubation, a defoaming agent such as vegetable oil, lard, or polypropylene glycol can be conveniently added to the medium, before or during the incubation.

After culturing, for the purpose of separating the compound of the present invention from the culture, an ordinary process of separating fermentation products is conveniently used. For example, filtration, centrifugation, absorption-elution or chromatography using various ion exchange resins or other active absorbents, extraction using various organic solvents can be adequately combined with each other.

The following describes physicochemical characters and structures of RD-01-compounds obtained through the above fermentation, incubation, and separation process.

RD-01-A$_3$     (a)

State: colorless amorphous powder (acidic and soluble substance in organic solvents such as ethyl acetate, acetone, methanol, and ethanol)

Molecular Formula: $C_{18}H_{19}O_9N$
Molecular Weight: 393
SIMS: m/z 394 [M+H]+.

UV Absorption Spectrum: $\lambda_{max}^{MeOH}$ ($E_{1\ cm}^{1\%}$) nm
MeOH: 215(930), 260(230), 305(70) 0.1N HCl-90%
MeOH: 215(770), 260(230), 303(70) 0.1N NaOH-90%
MeOH: 275(190), 317(100).

IR Absorption Spectrum: $\nu_{max}^{KBr}$ cm$^{-1}$ 3400, 3182, 2966, 1714, 1653, 1605, 1494, 1452, 1412, 1364, 1270, 1238, 1206, 1067, 978, 941, 769.

$^1$H-NMR: (200 MHz, d$_6$DMSO) ppm (J=Hz) 1.147(3H, d, J=7.0, CH$_3$); 1.8-2.4(2H, m); 2.235(2H, s); 2.725(1H, qd, J=7.0, 7.0); 2.975(1H, dd, J=7.5, 16.5); 3.2-3.4(1H, m); 4.246(2H, s); 4.750(1H, m); 5.020(1H, m); 6.494(1H, s).

$^{13}$C-NMR: (50 MHz, d$_6$DMSO) ppm 11.90(q), 24.13(t), 30.18(t), 30.64(t), 43.86(d), 44.72(t), 53.08(d), 84.22(d), 94.76(d), 117.22(s), 121.88(s), 133.18(s), 148.80(s), 161.22(s), 168.83(s), 172.44(s), 173.87(s), 174.90(s).

HPLC Column: COSMOSIL PACKED COLUMN 5C$_{18}$ (4.6Φ×150 mm) Solvent: acetonitrile: 0.1% TFA=13:87 Flow rate: 1 ml/min. Detection: UV(220 or 254 nm) Retention time: 12.1 min.
Structure:

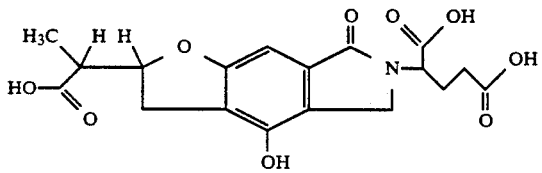

(b) RD-01-A$_4$

State: colorless fine needless (acidic and soluble substance in organic solvents such as ethyl acetate, acetone, methanol, and ethanol)

Molecular Formula: $C_{15}H_{15}O_7N$
Molecular Weight: 321
SIMS: m/z 322 [M+H]+
[α]$_D$: +46.3°±1.7°

Solubility: soluble in ethyl acetate, DMSO, methanol, and ethanol; slightly soluble in chloroform and ether; insoluble in petroleum ether.

UV Absorption Spectrum: $\lambda_{max}^{MeOH}$ ($E_{1\ cm}^{1\%}$) nm
MeOH: 215(810), 258(190), 303(60) 0.01N HCl-90%
MeOH: 215(710), 258(190), 303(60) 0.01N NaOH-90%
MeOH: 220 sh(630), 275(150), 316(60) (See FIG. 1.).

Figure 2:
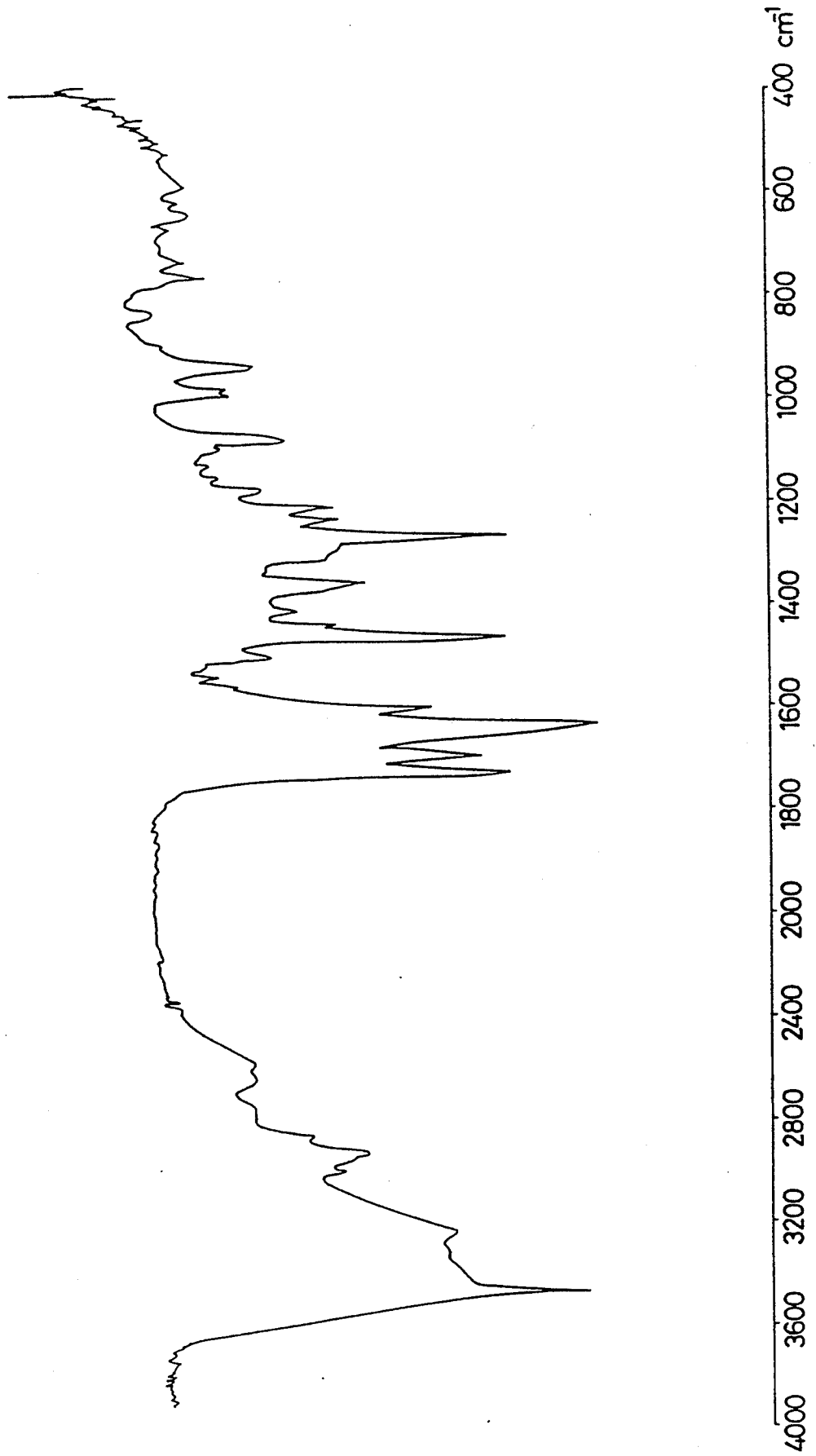
FIG. 2 is an IR spectrum of RD-01-A$_4$ of the present invention.

IR Absorption Spectrum: $\nu_{max}^{KBr}$ cm$^{-1}$ 3466, 3234, 2918, 1725, 1691, 1634, 1599, 1053, 1459, 1356, 1266, 1235, 1211, 1077, 992, 936 (See FIG. 2.).

$^1$H-NMR: (DMSO) ppm (J=Hz) 1.150(3H, d, J=7.0); 2.717(1H, qd, J=7.0, 7.0); 2.944(1H, dd, J=7.2, 16.6); 3.310(1H, dd, J=9.0, 16.6); 4.202(2H, s); 4.295(2H, s); 5.001(1H, ddd, J=7.0, 7.2, 9.0); 6.492(1H, s). (See FIG. 3.).

Figure 4:
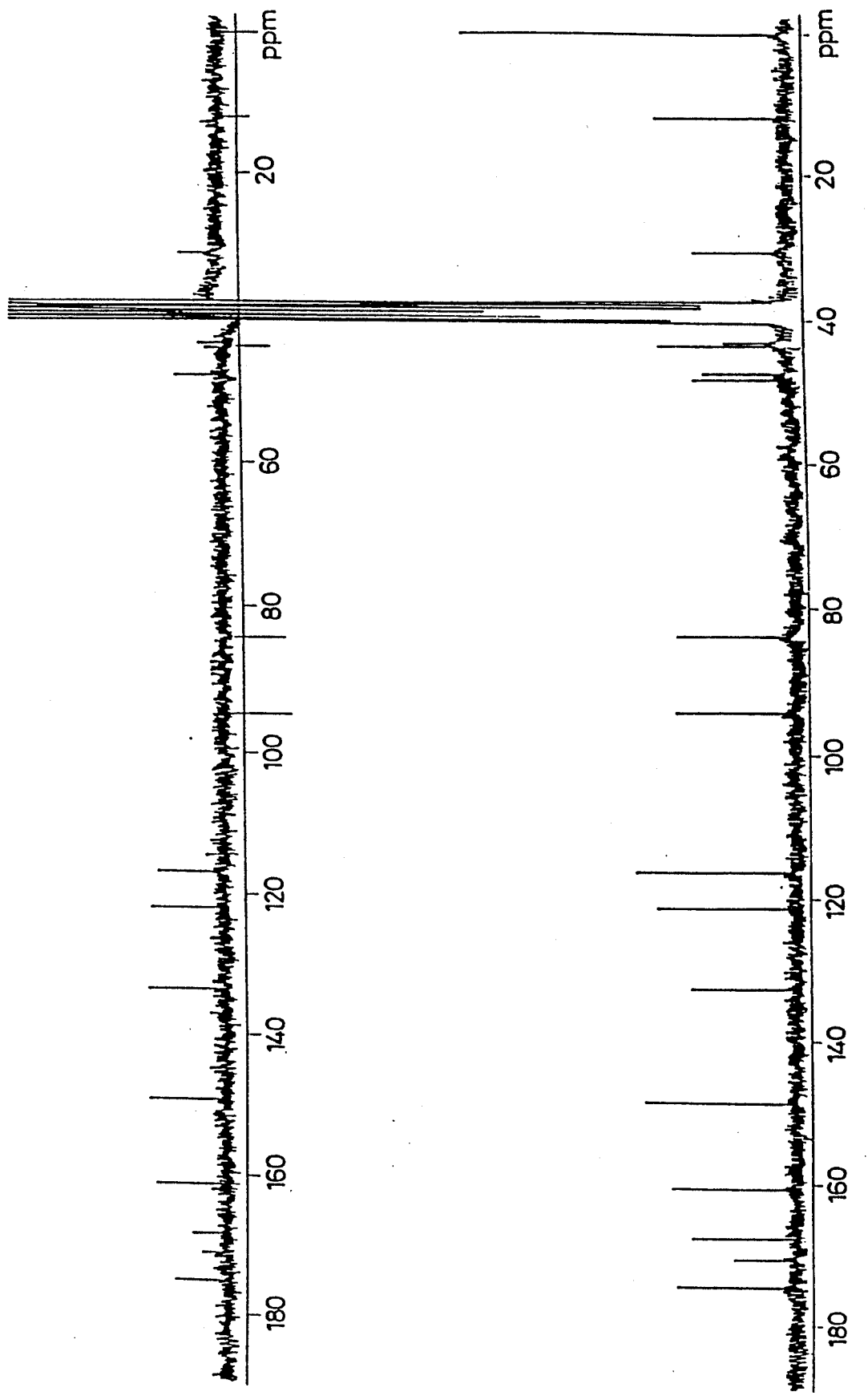
FIG. 4 is a $^{13}$C-NMR spectrum of RD-01-A$_4$ of the present invention.

$^{13}$C-NMR: (DMSO) ppm 12.17(q), 30.85(t), 43.67(t), 44.08(d), 47.95(t), 84.28(d), 94.64(d), 117.05(s), 121.88(s), 133.43(s), 148.93(s), 161.14(s), 168.13(s), 171.09 (s), 174.98(s). (See FIG. 4.).

Figure 5:
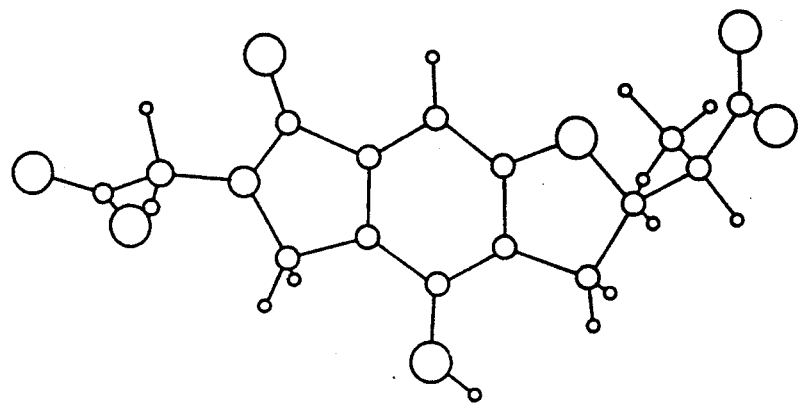
FIG. 5 is a diagram showing the results of X-ray analysis of RD-01-A$_4$ of the present invention.

X-ray Analysis: see FIG. 5.

HPLC Column: COSMOSIL 5C$_{18}$ (20Φ×150 mm) Solvent: acetonitrile: 0.1% TFA=15:85 Flow rate: 9 ml/min. Detection: UV(254 nm) Retention time: 21.4 min.
Structure:

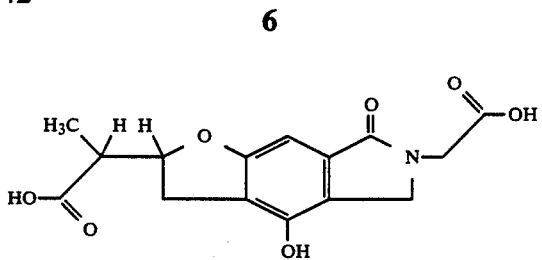

(c) RD-01-A$_7$

State: colorless fine needles (acidic and soluble substance in organic solvents such as ethyl acetate, acetone, methanol, and ethanol)

Molecular Formula: $C_{16}H_{17}O_7N$
Molecular Weight: 335
Melting Point: 293°-296° C. (decomp.)
SIMS: m/z 336 [M+H]+, m/z 358 [M+Na]+, m/z 671 [2M+H]+, m/z 693 [2M+Na]

UV Absorption Spectrum: same as that of RD-01-A$_3$ and RD-01-A$_4$.

IR Absorption Spectrum: no data.

$^1$H-NMR: (200 MHz, d$_6$DMSO) ppm (J=Hz) 1.141(3H, d, J=7.0); 1.468(3H, d, J=7.4); 2.711(1H, qd, J=7.0, 6.8); 2.967(1H, dd, J=7.4, 16.6); 3.2-3.4(1H, m); 4.243(2H, s); 4.768(1H, q, J=7.4); 5.002(1H, ddd, J=6.8, 7.4, indistinctness); 6.488(1H, s).

$^{13}$C-NMR: (50 MHz, d$_6$DMSO) ppm 12.56(q), 15.75(q), 31.24(t), 44.42(d), 44.92(t), 49.55(d), 84.51(d), 94.79(d), 117.20(s), 122.11(s), 133.71(s), 149.08(s), 161.24(s), 168.06(s), 173.52(s), 174.98(s).

HPLC Column: COSMOSIL PACKED COLUMN 5C$_{18}$ (4.6Φ×150 mm) Solvent: acetonitrile: 0.1% TFA=20:80 Flow rate: 1 ml/min. Detection: UV(220 or 254 nm) Retention time: 6.8 min.
Structure:

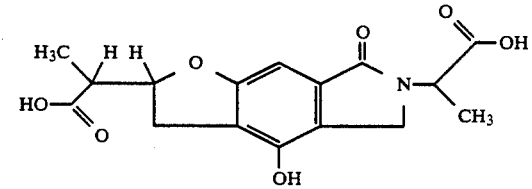

(d) RD-01-C$_1$

State: pale yellow amorphous powder (acidic and soluble substance in organic solvents such as ethyl acetate, acetone, methanol, and ethanol)

Molecular Formula: $C_{13}H_{11}O_6N$
Molecular Weight: 277
SIMS: m/z 278 [M+H]+, m/z 555 [2M+H]+, UV Absorption Spectrum: $\lambda_{max}^{MeOH}$($E_{1\ cm}^{1\%}$)nm MeOH: 223(670), 348(840), 335(110) 0.01N HCl-90% MeOH: 223(580), 348(770), 335(110) 0.01N NaOH-90% MeOH: 234(780), 247 sh(580), 393(150).

IR Absorption Spectrum: no data.

$^1$H-NMR: (200 MHz, CDCl$_3$) ppm (J=Hz) (This data is for trimethyl-derivative)* 1.333(3H, d, J=7.2); 2.825(1H, dq, J=7.2, 7.2); 3.070(1H, dd, J=7.6, 16.8); 3.106(3H, s); 3.419(H, dd, J=9.6, 16.8); 3.719(3H, s); 4.198(3H, s); 5.098(1H, ddd, J=7.2, 7.6, 9.6); 6.929(H, s).

$^{13}$C-NMR: (50 MHz, CDCl$_3$) ppm (This data is for trimethyl-derivative)* 13.04(q), 23.91(q), 31.70(t), 44.83(d), 52.11(q), 61.65(q), 85.51(d), 100.63(d), 112.44(s), 122.33(s), 136.66(s), 154.64(s) 165.70(s), 166.74(s), 167.72(s), 173.60(s).

*: As an amount of obtained RD-01-C$_1$ was very small, the structure of trimethyl-derivative of RD-01-C$_1$ was determined by $^1$H-NMR and $^{13}$C-NMR for it, then the structure of RD-01-C$_1$ was confirmed by SIMS.

HPLC Column: COSMOSIL PACKED COLUMN $_5$C$_{18}$ (4.6Φ×150 mm) Solvent: (acetonitrile: THF=8:2): 0.1% TFA=20:80 Flow rate: 1 ml/min. Detection: UV(200 or 254 nm) Retention time: 8.7 min.

Structure:

[Chemical structure diagram]

(e) RD-01-C$_2$

State: colorless fine needles (acidic and soluble substance in organic solvents such as ethyl acetate, acetone, methanol, and ethanol)

Molecular Formula: C$_{15}$H$_{13}$O$_8$N
Molecular Weight: 335
Melting point: 246°–247° C.
SIMS: m/z 336 [M+H]$^+$, m/z 671[2M+H]$^+$
UV Absorption Spectrum: $\lambda_{max}^{MeOH}$(E$_1$ $_{cm}$$^{1\%}$)nm
MeOH: 223(600), 247(900), 335(110) 0.01N HCl-90%
MeOH: 223(520), 247(870), 335(110) 0.01N NaOH-90%
MeOH: 241(900), 255 sh(600), 277 sh(60), 395(150), IR Absorption Spectrum: $\nu_{max}^{KBi}$ cm$^{-1}$ 3100, 2984, 2948, 2648, 2566, 1696, 1613, 1498, 1457, 1425, 1387, 1358, 1299, 1277, 1250, 1198, 1115, 1099, 1049, 1020, 994, 935, 865, 823, 803, 756, 704, 674, 655, 619, 585, 546, 512.

$^1$H-NMR: (200 MHz, d$_6$DMSO) ppm (J=Hz) 1.152(3H, d, J=7.0); 2.798(1H, dq, J=7.0, 7.0); 3.016(1H, dd, J=7.4, 16.8); 3.2-3.4(1H, m); 4.190(2H, s); 5.165(1H, ddd, J=7.0, 7.4, indistinctness); 6.775(1H, s).

$^{13}$C-NMR: (50 MHz, d$_6$DMSO) ppm 11.86(q), 30.44(t), ca 38(t), 43.69(d), 85.44(d), 97.49(d), 109.10(s), 119.76(s), 134.78(s), 152.12(s), 165.57(s), 165.69(s), 166.60(s), 169.05(s), 174.21(s).

HPLC Column: COSMOSIL PACKED COLUMN $_5$C$_{18}$ (4.6 Φ×150 mm) Solvent: (acetonitrile: THF=8:2): 0.1% TFA=20:80 Flow rate: 1 ml/min. Detection: UV(220 or 254 nm) Retention time: 12.6 min.

Structure:

[Chemical structure diagram]

(f) RD-01-C$_3$

State: pale yellow oil (acidic and soluble substance in organic solvents such as ethyl acetate, acetone, methanol, and ethanol)

Molecular Formula: C$_{16}$H$_{15}$O$_8$N
Molecular Weight: 349

Melting point: 246°–247° C.
SIMS: m/z 350 [M+H]$^+$, m/z 372 [M+Na]$^+$, m/z 699 [2M+H]$^+$, m/z 721 [2M+Na]$^+$ UV Absorption Spectrum: same as that of RD-01-C$_1$ and RD-01-C$_2$ IR Absorption Spectrum: no data $^1$H-NMR: (200 MHz, d$_6$DMSO) ppm (J=Hz) 1.143(3H, d, J=7.0); 1.490(3H, d, J=7.3); 2.788(1H, qd, J=7.0, 7.0); 3.006(1H, dd, J=7.3, 16.6); 3.2–3.4(1H, m); 4.739(1H, q, J=7.3); 5.165(1H, ddd, J=7.0, 7.3, indistinctness); 6.746(1H, s).

$^{13}$C-NMR: (50 MHz, d$_6$DMSO) ppm 11.81(q), 14.90(q), 30.46(t), 43.79(d), 46.46(d), 85.61(d), 97.63(d), 109.22(s), 120.02(s), 135.03(s), 152.47(s), 165.98(s), 166.08(s), 166.91(s), 171.65(s), 174.66(s).

HPLC Column: COSMOSIL PACKED COLUMN $_5$C$_{18}$ (4.6Φ×150 mm) Solvent: (acetonitrile: THF=8:2): 0.1% TFA=22:78 Flow rate: 1 ml/min. Detection: UV(220 or 254 nm) Retention time: 16.0 min.

Structure:

[Chemical structure diagram]

Moreover, if necessary, alkylation can be conducted by normal methods to form the compound of the present invention wherein R$^1$, R$^2$, R$^3$, and R$^4$ are the same or different from each other.

The following will describe methods for producing these compounds in brief. Compounds of the aforesaid formula (B) are obtained through the above fermentation, incubation and separation process, and among them, the compound wherein R is not hydrogen is named Compound I, the compound wherein R is hydrogen is named Compound i.

(1) A mixture of Compound II having hydrogen as R$^1$ and the same alkyl groups R$^2$ and R$^3$ and Compound VIII having hydrogens as R$^1$ and R$^2$ and an alkyl group as R$^3$ in aforesaid formula (A) can be obtained by mixing above Compound I with an alkanol (such as ethanol) and an organic or inorganic acid and by refluxing the mixture for about 1 hour to about 2 hours. The mixture is separated by suitable means to yield either Compound II or Compound VIII.

Examples of the organic or inorganic acid include hydrochloric acid, sulfuric acid, toluenesulfonic acid, boron trifluoride, and acetic anhydride.

Compound II and Compound VIII are also synthesized by dissolving Compound I in an appropriate solvent such as a tetrahydrofuran(THF)-ether system, adding diazoalkane such as diazomethane, and allowing the solution to stand at room temperature for several minutes to several tens of minutes.

(2) A compound having alkyl groups as R$^1$, R$^2$, and R$^3$ can be obtained by dissolving Compound II in an appropriate solvent such as N,N-dimethylformamide (DMF) and acetone and allowing the solution to react with alkyl iodide such as methyl iodide in the presence of alkali such as potassium carbonate or catalyst such as silver oxide at about 30° C. to about 100° C. for about 30 minutes to about 3 hours.

In this reaction, Compound III having the same alkyl groups $R^1$, $R^2$, and $R^3$ can be synthesized by using alkyl iodide which has the same alkyl as $R^2$ and $R^3$ of Compound II, and Compound III having a different alkyl group $R^1$ from $R^2$ and $R^3$ can be synthesized by using alkyl iodide which has a different alkyl from $R^2$ and $R^3$ of Compound II.

Compound III can also be obtained by allowing Compound I to react with alkyl iodide as mentioned above or by dissolving Compound I in an appropriate solvent such as a THF-ether system, adding diazoalkane, and allowing the solution to stand at room temperature for several hours to overnight.

Compound iii having the same alkyl groups $R^1$, $R^2$ and $R^4$ can be obtained by treating Compound i with alkyl iodide or diazoalkane as mentioned above.

(3) Compound IV having hydrogen as $R^3$ and the same alkyl groups $R^1$ and $R^2$ can be obtained by partial hydrolysis of esters of Compound IV, which comprises mixing Compound III with several percent to several tens of percent methanol and several tens of percent alkali aqueous solution such as potassium carbonate and stirring at room temperature for several tens of minutes to several hours.

Compound IV' having hydrogen as $R^3$ and different alkyl groups $R^1$ and $R^2$ from each other can be synthesized by partial hydrolysis of esters of Compound III' in the same way as aforesaid.

(4) Compound V having hydrogen as $R^2$ and $R^3$ and an alkyl group as $R^1$ can be obtained by hydrolysis of esters of Compound III, Compound III' or Compound IV', which comprises mixing Compound III, Compound III' or Compound IV' with several percents to several tens of percents methanol and several tens of percent potassium carbonate and allowing the mixture to react at 30° C. to 80° C.

(5) A mixture of a compound having alkyl groups as $R^1$, $R^2$ and $R^3$ and a compound having hydrogen as $R^2$ and alkyl groups as $R^1$ and $R^3$ can be obtained by treating Compound V with alkanol or diazoalkane as mentioned in (1).

In this reaction, a mixture of Compound III having the same alkyl groups $R^1$, $R^2$ and $R^3$ and Compound VI having hydrogen as $R^2$ and the same alkyl groups $R^1$ and $R^3$ can be obtained by using alkanol or diazoalkane which has the same alkane as $R^1$ of Compound V, and a mixture of Compound III' having the same alkyl groups $R^2$ and $R^3$ which are different from an alkyl group $R^1$ and Compound VI having hydrogen as $R^2$ and different alkyl groups $R^3$ and $R^1$ from each other can be obtained by using alkanol or diazoalkane which has a different alkane from $R^1$ of Compound V.

Compound III, Compound III', Compound VI, and Compound VI' each is isolated by separating their mixtures with the use of suitable means.

Compound vi having hydrogen as $R^2$ and the same alkyl groups $R^1$ and $R^4$ can be synthesized by hydrolyzing esters of Compound iii as mentioned in (4).

(6) Compound VII having hydrogens as $R^1$ and $R^3$ and an alkyl group as $R^2$ can be obtained by hydrolyzing esters of Compound II with the use of methanol and alkaline at room temperature for several hours as mentioned in (3).

Compound vii having hydrogen as $R^1$ and $R^4$ and an alkyl group as $R^2$ can be obtained by mixing Compound i with alkanol such as ethanol and an organic or inorganic acid and by refluxing the mixture for about 1 hour to 2 hours.

(7) Compound II' having hydrogen as $R^1$ and different alkyl groups $R^2$ and $R^3$ from each other can also be obtained by dissolving Compound VII or Compound VIII in an appropriate solvent such as a THF-ether system, adding diazoalkane which has a different alkane from $R^2$ or $R^3$ of Compound VII or Compound VIII, and allowing the mixture to stand at room temperature for several minutes to several tens of minutes, or by mixing Compound VII or Compound VIII with alkanol which has a different alkane from $R^2$ or $R^3$ of Compound VII or Compound VIII and an organic or inorganic acid, and refluxing the mixture at room temperature for about 1 hour to about 2 hours.

(8) A compound having the same alkyl groups $R^1$ and $R^2$ and a different alkyl group $R^3$ from $R^1$ and $R^2$ can be synthesized by allowing Compound IV to react with diazoalkane or alkanol which has a different alkane from $R^1$ and $R^2$ of Compound IV in the same means as above (7), a compound having the same alkyl groups $R^1$ and $R^3$ and a different alkyl group $R^2$ from $R^1$ and $R^3$ can be synthesized by allowing the Compound VI to react as mentioned above, and a compound having different alkyl groups $R^1$, $R^2$, and $R^3$ from each other can also be obtained by treating Compound IV' or Compound VI' with alkanol or diazoalkane which has a different alkane from $R^1$ and $R^2$ of Compound IV' or $R^1$ and $R^3$ of Compound VI'.

Furthermore, a compound having the same alkyl groups $R^1$ and $R^4$ and a different alkyl group $R^2$ from $R^1$ and $R^4$ can be obtained by treating Compound vii with diazoalkane which has a different alkane from $R^2$ of Compound vii, or with alkyl iodide which has a different alkyl from $R^2$ of Compound vii as mentioned in (2). This compound can also be synthesized by treating Compound vi with alkanol which has a different alkyl from $R^1$ and $R^4$ of Compound vi.

The following describes physicochemical characters and structures of RD-01-Compounds methylated in accordance with above alkylation process.

(a) Tetramethyl RD-01-A$_3$

Molecular Formula: $C_{22}H_{27}O_9N$

Molecular Weight: 449

SIMS: m/z 450 $[M+H]^+$, m/z 472 $[M+Na]^+$ $^1$H-NMR: (200 MHz, CDCl$_3$) ppm (J=Hz) 1.340(3H, d, J=7.2); 2.1–2.5(4H, m); 2.813(1H, dq, J=7.2, 7.2); 3.151(1H, dd, J=7.4, 16.0); 3.498(1H, dd, J=9.3, 16.0); 3.618(3H, s); 3.718(3H, s); 3.726(3H, s); 3.983(3H, s); 4.317(1H, d, J=16.2); 4.496(1H, d, J=16.2); 4.9–5.1(2H, m); 6.914(1H, s).

$^{13}$C-NMR: (50 MHz, CDCl$_3$) ppm 13.28(q), 25.04(t), 30.68(t), 32.49(t), 44.89(d), 45.11(t), 51.80(q), 51.99(q), 52.45(q), 53.29(q), 58.59(q), 84.16(d), 98.82(d), 119.00(s), 123.56(s), 133.81(s), 151.16(s), 161.79(s), 168.74(s), 171.12(s), 172.81(s), 173.99(s).

Structure:

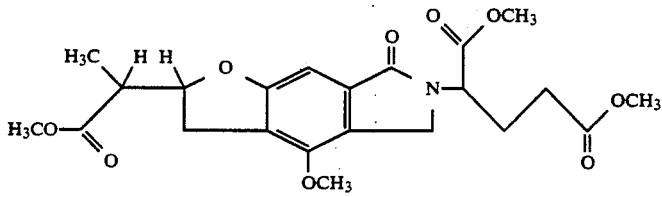

(b) Trimethyl RD-01-A$_4$

Molecular Formula: $C_{18}H_{21}O_7N$
Molecular Weight: 363
$^1$H-NMR: (CDCl$_3$) ppm (J=Hz) 1.342(3H, d, J=7.2, 11-CH$_3$); 2.818(1H, qd, J=7.2, 7.2, 11-H); 3.138(1H, dd, J=7.2, 16.2, 3-H); 3.489(1H, dd, J=9.2, 16.2, 3-H); 4.998(1H, ddd, J=7.2, 7.2, 9.2, 2-H); 4.378(2H, s); 4.468(2H, s); 6.933(1H, s, 8-H); 3.714(3H, s, COOCH$_3$); 3.758(3H, s, COOCH$_3$); 3.971(3H, s, 4-OCH$_3$).
Structure:

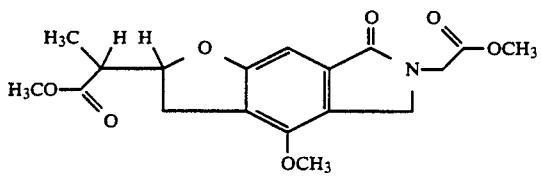

(c) Trimethyl RD-01-C$_1$

Molecular Formula: $C_{16}H_{17}O_6N$
Molecular Weight: 319
SIMS: m/z 320 [M+H]$^+$, m/z 639 [2M+H]$^+$ (m/z 320 in HR-SIMS means $C_{16}H_{18}O_6N$).
$^1$H-NMR: (200 MHz, CDCl$_3$) ppm (J=Hz) 1.333(3H, d, J=7.2); 2.825(1H, dq, J=7.2, 7.2); 3.070(H, dd, J=7.6, 16.8); 3.106(3H, s); 3.419(1H, dd, J=9.6, 16.8); 3.719(3H, s); 4.198(3H, s); 5.098(1H, ddd, J=7.2, 7.6, 9.6); 6.929(1H, s).
$^{13}$C-NMR: (50 MHz, CDCl$_3$) ppm 13.04(q), 23.91(q), 31.70(t), 44.83(d), 52.11(q), 61.65(q), 85.51(d), 100.63(d), 112.44(s), 122.33(s), 136.66(s), 154.64, 165.70(s), 166.74(s), 167.72(s), 173.60(s).
Structure:

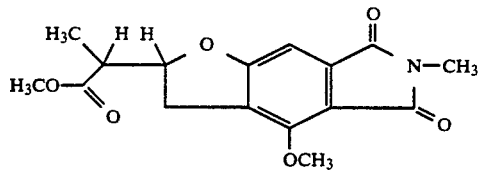

(d) Trimethyl RD-01-C$_2$

Molecular Formula: $C_{18}H_{19}O_8N$
Molecular Weight: 377
SIMS: m/z 378 [M+H]$^+$, m/z 755 [2M+H]$^+$
$^1$H-NMR: (200 MHz, CDCl$_3$) ppm (J=Hz) 1.340(3H, d, J=7.0); 2.837(1H, dq, J=7.0, 7.0); 3.088(1H, dd, J=7.8, 16.8); 3.447(1H, dd, J=9.8, 16.8); 3.731(3H, s); 3.761(3H, s); 4.210(3H, s); 4.382(2H, s); 5.125(1H, ddd, J=7.0, 7.8, 9.8); 6.972(1H, s).
$^{13}$C-NMR: (50 MHz, CDCl$_3$) ppm 13.45(q), 32.17(t), 39.20(t), 45.26(d), 52.58(q), 53.07(q), 62.12(q), 86.05(d), 101.43(d), 112.62(s), 123.15(s), 136.82(s), 155.45(s), 166.11(s), 166.46(s), 167.21(s), 168.43(s), 174.01(s).

Structure:

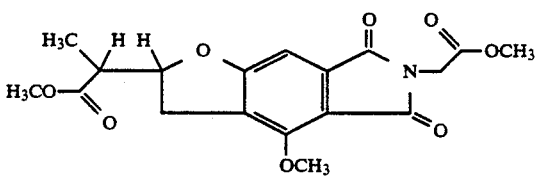

When an agent for inhibiting an aldose reductase of the present invention is administered to patients, the daily dose is 1 mg to 1000 mg, preferably 100 mg to 500 mg, although it depends on sex, age, and the condition of patients. The preferable route of dosage is oral, though either oral or non-oral route can be taken. Agent forms used in the oral administration involves elixirs, capsules, granules, pills, suspensions, emulsions, powders, tablets, and syrups, but tablets are better than the others.

Tablets can be prepared by usual methods for tablets as follows. An aldose reductase inhibitor according to this invention is first rendered granular with or without uniform admixture with a diluent, binder, disintegrator, and other suitable additives. The resultant granules are provided with additives such as a lubricant, and compressed into a desired shape and size. These granules are usually prepared by compressing a drug of the above mixtures and crushing to granules, granulating and drying. Tablets may also be prepared either by direct compression of a drug with or without a diluent, binder, disintegrator, and other suitable additives, or by compression after drugs with or without suitable additives have been added to previously prepared inactive granules. If necessary, coloring agents, flavoring agents, etc. may be added. Tablets may be coated with sucrose or other suitable coating agents.

The following will show the embodiments of the present invention as examples, but these are not intended to restrict the present invention.

EXAMPLE 1

(1) Culturing Step

A slant culture of the Crucibulum RF-3817 is used to seed a 500 ml-Erlenmeyer flask charged with 100 ml of a medium which is composed of 20 g of potato starch, 20 g of sucrose, 5 g of yeast extract, and 1000 ml of service water (with an unadjusted pH) and a shake culture is performed at 28° C. and 180 rpm for 5 days. Four ml of the culture medium is used to inoculate each of one hundred 500 ml-Erlenmeyer flasks charged with 100 ml of a medium which is composed of 20 g of potato starch, 20 g of sucrose, 5 g of yeast extract, and 1000 ml of service water (with an unadjusted pH) and shake cultures are performed at 28° C. and 180 rpm for 10 to 15 days.

(2) Separating and Purifying Step

Mycelia are removed from 8 L of the culture medium by filtration. The filtrate (about 8 L) is adjusted to pH 2 by the addition of 2N HCl and then extracted twice with 3 L of ethyl acetate. The ethyl acetate layer is washed with saturated saline and dried by anhydrous sodium sulfate, followed by vacuum distillation, resulting in 4.422 g of crude extract. The crude extract is dissolved in a mixture of acetonitrile and 0.1% TFA in a ratio of 8:2, and the resulting solution is placed on a column of MCI GEL CHP-20P (75 to 150μ, 200 ml) previously equilibrated with the same mixture. The column is eluted with a concentration gradient consisting of mixtures of acetonitrile and 0.1% TFA in a ratio of 20:80 to 80:20. As a result, fraction 1, fraction 2, fraction 3, fraction 4, and fraction 5 were separated. From fraction 1 was obtained 222 mg of $RD-01-A_3$ crude product, 954 mg of a mixture of $RD-01-A_3$ crude product and $RD-01-A_4$ crude product was from fraction 2, 314 mg of $RD-01-A_7$ crude product was from fraction 3, 467 mg of a mixture of $RD-01-C_1$ crude product and $RD-01-C_2$ crude product was from fraction 4, and 1.361 g of $RD-01-C_3$ crude product was from fraction 5.

(a) Isolation of $RD-01-A_3$ and $RD-01-A_4$

The mixture obtained from fraction 2 is further separated and purified by chromatography (column; LiCroprep PR-18, 25 to 40μ, 20Φ×500 mm, solvent; acetonitrile: 0.1% TFA=13:87), resulting in 183 mg of $RD-01-A_3$ colorless amorphous powder and 145 mg of $RD-01-A_4$ purified product.

$RD-01-A_4$ purified product is further recrystallized from 50% isopropanol to yield 77 mg of colorless fine needles.

(b) Isolation of $RD-01-A_7$

The crude products obtained from fraction 3 is further separated and purified by column chromatography (column; LiCroprep PR-18, 25 to 40μ, 20Φ×500 mm, solvent; (acetonitrile: THF=8:2): 0.1% TFA=13:87), resulting in 167 mg of $RD-01-A_7$ purified product. The purified product is further recrystallized from 50% methanol to yield 69 mg of colorless fine needles.

(c) Isolation of $RD-01-C_1$ and $RD-01-C_2$

The mixture obtained from fraction 4 is further separated and purified by column chromatography (column; LiCroprep PR-18, 25 to 40μ, 20Φ×500 mm, solvent; acetonitrile: 0.1% TFA=20:80), resulting in 29 mg of $RD-01-C_1$ purified product and 59 mg of $RD-01-C_2$ purified product.

$RD-01-C_1$ product (29 mg) is further separated and purified by HPLC (column; COSMOSIL-5-C18, 20Φ×150 mm, solvent; acetonitrile: 0.1% TFA=20:80) to yield 7 mg of pale yellow amorphous powder.

$RD-01-C_2$ product (59 mg) is also separated and purified by HPLC (column; COSMOSIL-5-C18, 20Φ×150 mm, solvent; acetonitrile: 0.1% TFA=20:80) and resulting purified product (25 mg) is further recrystallized from 50% isopropanol to yield 13 mg of colorless fine needles.

(d) Isolation of $RD-01-C_3$

The crude products obtained from fraction 5 is further separated and purified by column chromatography (column; LiCroprep PR-18, 25 to 40μ, 20Φ×500 mm, solvent; acetonitrile: 0.1% TFA=20:80), resulting in 68 mg of $RD-01-C_3$ purified product. The purified product is further separated and purified by HPLC (column; COSMOSIL-5-C18, 20Φ×150 mm, solvent; (acetonitrile: THF=8:2): 0.1% TFA=23:77) to yield 12 mg of pale yellow oil.

(3) Methylation of RD-01-Compounds

(a) Synthesis of tetramethyl $RD-01-A_3$

To 0.5 ml methanol solution of 17 mg of $RD-01-A_3$ purified product obtained in Example 1, 0.2 ml of trimethylsilyldiazomethane (10% n-hexane solution) is added four times every one hour (the total amount: 0.8 ml). The resulting mixture is allowed to stand overnight at room temperature, followed by evaporation to dryness after adding a drop of acetic acid. The sample was subjected to TLC (Merck silica gel 60 F254 pre-coated (0.5 mm), toluene and ethyl acetate (1:1) solution system; UV detection). The fraction with an Rf value of 0.4 was extracted with a toluene acetate ester system, resulting in 10 mg of the tetramethyl $RD-01-A_3$, which was identified by $^1$H-NMR, $^{13}$C-NMR and SIMS as a methyl ether trimethyl ester of $RD-01-A_3$ obtained in Example 1.

(b) Synthesis of trimethyl $RD-01-A_4$

To 0.5 ml methanol solution of 5.9 mg of $RD-01-A_4$ purified product obtained in Example 1, an excessive amount of trimethylsilyldiazomethane (10% n-hexane solution) is added, and the resulting mixture is allowed to stand overnight at room temperature, followed by evaporation to dryness. The sample was subjected to TLC (Merck KGF, toluene and ethyl acetate (1:1) solution system; UV detection). The fraction with an Rf value of 0.3 was extracted with a toluene acetate ester system and evaporated to dryness, resulting in 3.5 mg of the trimethyl $RD-01-A_4$, which was identified by $^1$H-NMR as a methyl ether dimethyl ester of $RD-01-A_4$ obtained in Example 1.

(c) Synthesis of trimethyl $RD-01-C_1$

To 1.0 ml methanol solution of 5.5 mg of $RD-01-C_1$ purified product obtained in Example 1, 1.0 ml of trimethylsilyldiazomethane (10% n-hexane solution) is added, and the resulting mixture is allowed to stand at room temperature for 2.5 hours, followed by evaporation to dryness after adding a drop of acetic acid. The sample was subjected to TLC (Merck silica gel 60 F254 pre-coated (0.5 mm), toluene and ethyl acetate (1:1) solution system; UV detection). The fraction with an Rf value of 0.6 was extracted with a toluene acetate ester system, resulting in 4.1 mg of the trimethyl $RD-01-C_1$, which was identified by $^1$H-NMR, $^{13}$C-NMR and SIMS as a methyl ether dimethyl ester of $RD-01-C_1$ obtained in Example 1.

(d) Synthesis of trimethyl $RD-01-C_2$

To 1.0 ml methanol solution of 7.6 mg of $RD-01-C_2$ purified product obtained in Example 1, 1.0 ml of trimethylsilyldiazomethane (10% n-hexane solution) is added, and the resulting mixture is allowed to stand at room temperature for 2 hours, followed by evaporation to dryness after adding a drop of acetic acid. The sample was subjected to TLC (Merck silica gel 60 F254 pre-coated (0.5 mm), toluene and ethyl acetate (1:1) solution system; UV detection). The fraction with an Rf value of 0.6 was extracted with a toluene acetate ester system, resulting in 6.3 mg of the trimethyl RD-01-C$_2$, which was confirmed identified, $^{13}$C-NMR and SIMS as a methyl ether dimethyl ester of RD-01-C$_2$ obtained in Example 1.

EXPERIMENTAL EXAMPLE

Aldose Reductase-Inhibiting Activity

Procedure

A homogenate of rat lenses was used as an enzyme source, glyceroaldehyde as a substrate, and TPNH as a coenzyme. To a mixture of 0.1M phosphate buffer (pH 6.2), 0.4M sodium sulfate, 0.1 mM TPNH (reduced form of triphosphopyridine nucleotide), and 10 mM D, L-glyceroaldehyde, a supernatant obtained from the homogenate of rat lenses by centrifugation was added as an enzyme source, so that the change in absorbance at 340 nm became 0.02 units per minute at 25° C. The change in absorbance at 340 nm for initial one minute was measured at 25° C., and the inhibiting activity was determined. The results was showed in Table 1.

TABLE 1

| | IC$_{50}$ ($\mu$g/ml) |
|---|---|
| RD-01-A$_3$ | 4.7 |
| RD-01-A$_4$ | 0.4 |
| RD-01-A$_7$ | 1.5 |
| RD-01-C$_1$ | 1.5 |
| RD-01-C$_2$ | 0.15 |
| RD-01-C$_3$ | 0.7 |

We claim:

1. A compound of the formula:

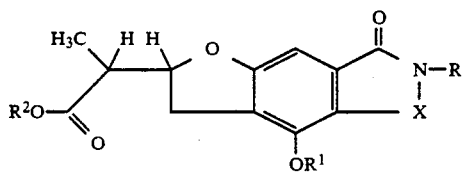

wherein
X is methylene or carbonyl;
R is

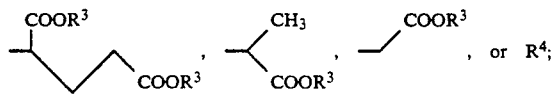

R$^1$, R$^2$, R$^3$, and R$^4$ each is hydrogen or lower alkyl, or the salt thereof.

2. The compound of claim 1 wherein R is

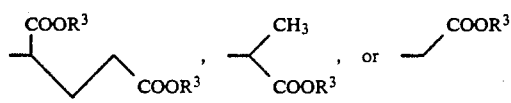

where
X is methylene;
R is

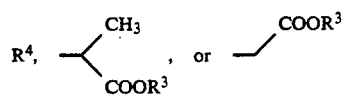

where X is carbonyl, or the salt thereof.

3. The compound of claim 1 wherein R$^3$ or R$^4$ is hydrogen, or salt thereof.

4. A method for producing the compound of claim 1, which comprises culturing Crucibulum sp. RF-3817 which can produce a compound of the formula:

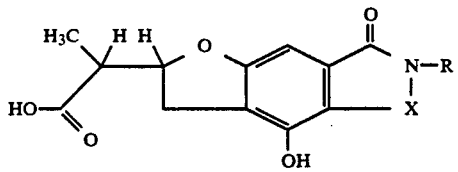

wherein R is

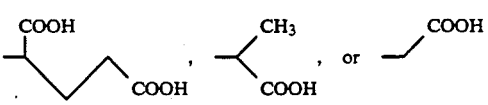

where
X is methylene;
R is

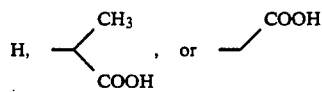

where X is carbonyl;
isolating said compound from the cultured medium and optionally alkylating said compound.

5. A pharmaceutical agent comprising a compound of claim 1, as an effective ingredient, in association with a pharmaceutically acceptable, nontoxic carrier or excipient.

6. A method for inhibiting aldose reductase comprising administering an aldose reductase inhibiting amount of the agent of claim 5.

7. The compound of claim 1, 2 or 3 wherein said compound is in a purified form.

8. The compound of claim 1, 2 or 3 wherein said compound is a purified product in a crystalline form.

9. A method for inhibiting aldose reductase which comprises administering an effective aldose reductase-inhibiting amount of the compound of claim 1 to a patient.

10. The method of claim 9, wherein said patient is a diabetic.

11. The method of claim 10, wherein said diabetic patient is suffering from a complication selected from the group consisting of diabetic neuropathy, diabetic cataract, diabetic keratopathy, diabetic retinopathy and diabetic nephropathy.

* * * * *

UNITED STATES PATENT AND TRADEMARK OFFICE
CERTIFICATE OF CORRECTION

PATENT NO. : 5,324,742
DATED : June 28, 1994
INVENTOR(S) : Yoshida et al.

Figures 3A, 3B:
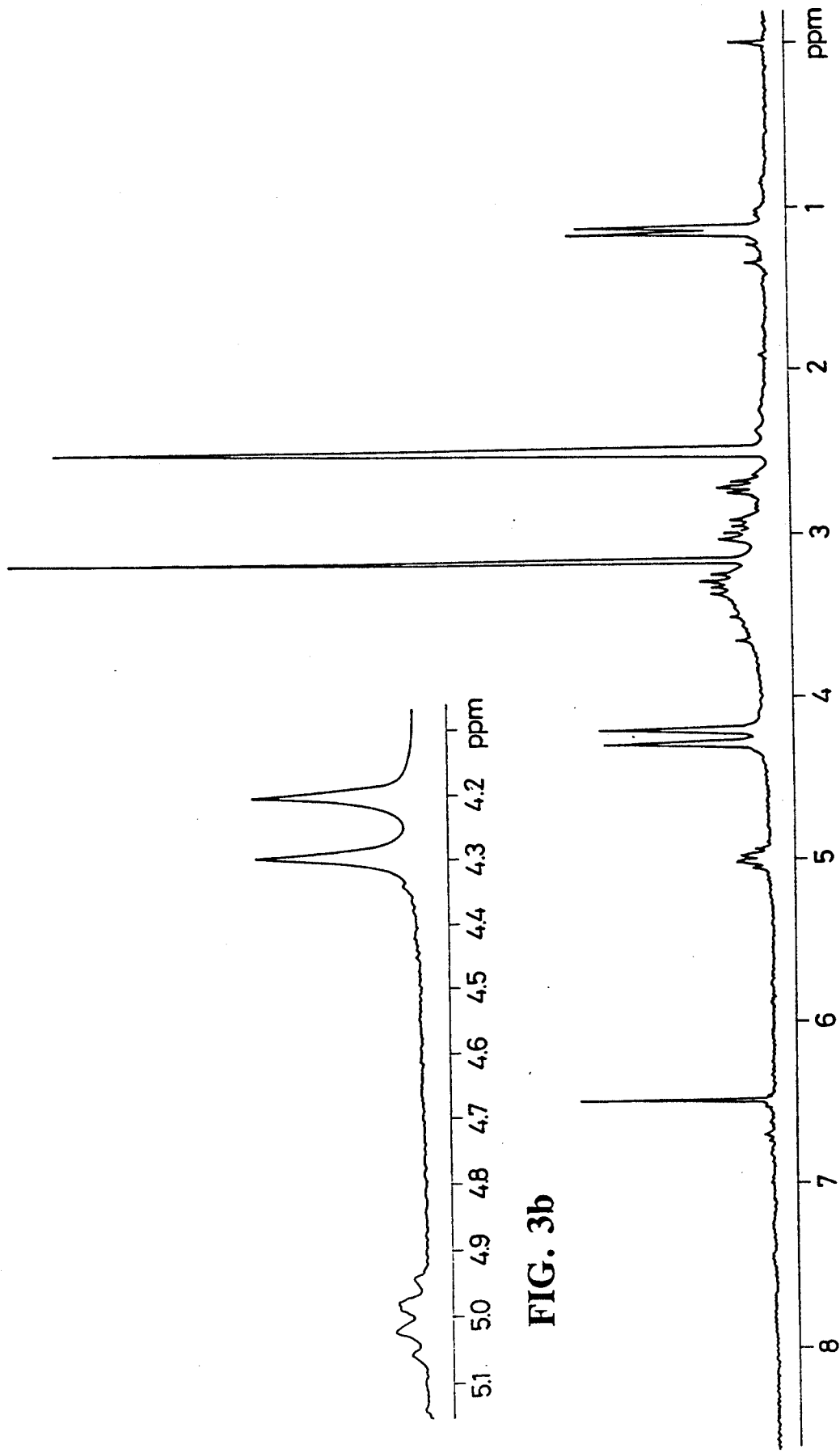
FIG. 3 is a $^1$H-NMR spectrum of RD-01-A$_4$ of the present invention.

It is certified that error appears in the above-indentified patent and that said Letters Patent is hereby corrected as shown below:

Column 3, line 37, change "Fig. 3" to read --Fig. 3a--;

Column 3, line 38, after "invention" insert --and Fig. 3b is an expansion of the region between 4.1 and 5.2 ppm of Fig. 3a--.

Signed and Sealed this

Twentieth Day of February, 1996

Attest:

BRUCE LEHMAN

*Attesting Officer*  *Commissioner of Patents and Trademarks*